United States Patent [19]

Sundermeyer et al.

[11] 3,957,839

[45] May 18, 1976

[54] METHOD FOR THE PREPARATION OF METHYLTIN TRICHLORIDE

[75] Inventors: Wolfgang Sundermeyer, Neckargemuend; Axel von Rumohr, Dossenheim; Willi Towae, Heidelberg; Max Buschhoff, Luenen, all of Germany

[73] Assignee: Schering Aktiengesellschaft, Berlin and Bergkamen, Germany

[22] Filed: Nov. 26, 1974

[21] Appl. No.: 527,482

[30] Foreign Application Priority Data

May 28, 1974 Germany............................ 2425770

[52] U.S. Cl. ............................................. 260/429.7
[51] Int. Cl.² ............................................. C07F 7/22
[58] Field of Search ................................. 260/429.7

[56] References Cited
UNITED STATES PATENTS

| | | | |
|---|---|---|---|
| 3,340,283 | 7/1967 | Gloskey | 260/429.7 |
| 3,414,595 | 12/1968 | Oakes | 260/429.7 |
| 3,415,857 | 12/1968 | Hoye | 260/429.7 |
| 3,446,826 | 5/1969 | Coates et al. | 260/429.7 |
| 3,519,667 | 7/1970 | Molt et al. | 260/429.7 |

OTHER PUBLICATIONS

Pfeiffer, Ber. Vol. 37, pp. 4618–4619 (1904).

Tchakirian et al., Compt. Rendus. V 2o2 pp. 138–140 (1936).

Gilman et al., J. Org. Chem. V 16, pp. 473 and 475 (1951).

Smith et al., J.A.C.S. V 75, pp. 4103–4106 (1953).

*Primary Examiner*—Helen M. S. Sneed
*Attorney, Agent, or Firm*—Curtis, Morris & Safford

[57] ABSTRACT

Method for making methyltin trichloride by reacting methyl chloride with molten tin-(II)-chloride in a salt melt comprising one or more chlorides of certain metals.

8 Claims, No Drawings

METHOD FOR THE PREPARATION OF METHYLTIN TRICHLORIDE

The present invention relates to a method for the preparation of methyltin trichloride.

Methyltin trichloride is an important precursor for the preparation of polyvinyl chloride stabilizers.

The introduction of alkyl groups onto the tin atom involves either a transfer of alkyl groups (the reaction of $SnCl_4$ with other suitable organometallic compounds, including alkyltin compounds themselves) or a redox reaction (the reaction of Sn or $SnCl_2$ with alkyl halides).

The introduction of only one alkyl group onto the tin atom by way of an alkyl transfer has, until now, only been successful in the case of $C_2H_5SnCl_3$, which is prepared from $SnCl_4$ and $(C_2H_5)_2Al(Oi-C_3H_7)$. [W. P. Neumann, Ann, Chem. 653, 163 (1962)].

The introduction of only one alkyl group onto the tin atom by means of the so-called comproportionation (alkyl transfer with alkyl tin compounds themselves as the organometallic component) according to the reaction

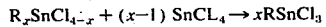

$$R_xSnCl_{4-x} + (x-1) SnCl_4 \rightarrow xRSnCl_3$$

(x = 4,3,2) is successful with only a few alkyl groups or takes place only in special solvents. [W. P. Neumann, "Die organische Chemie des Zinns", Ferdinand Enke Verlag, Stuttgart, pages 41–43 (1967)].

The introduction of only one alkyl group onto the tin atom by way of a redox reaction has been demonstrated, for example, for $CH_3SnI_3$. [P. Pfeiffer et al., Ber. dtsch. chem. Ges. 37, 4618 (1904)]. Alkali halide complexes of $SnCl_2$ have also been employed for this reaction [A. Tschakirian et al., Chem. Zentralbl. 1936, 3671; R. W. Leeper, Iowa State Coll. J. Sci. 18, 57–59 (1943), C.A. 38, 727 (1944)]. For the reaction of $SnCl_2$ with alkali chlorides, catalysts (cf. British Pat. No. 1,146,435, British Pat. No. 1,064,178, U.S. Pat. No. 3,519,667, German Auslegeschrift No. 1,259,889, or German Offenlegungsschrift No. 2,228,855) or high temperatures [A. C. Smith, Jr. et. al., Journ. Amer. Chem. Soc. 75, 4103–4106 (1953)] are necessary.

As catalysts for the reaction of $SnCl_2$ with $CH_3Cl$, mercaptans, alcohols, amines, phosphines, ammonium salts or phosphonium salts, organoantimony compounds, or metal salts have been used, for example. Because of the requirement for high purity, which is increasingly demanded in polyvinyl chloride stabilizers, the catalysts must be separated from the reaction product. This means additional costs which render the catalytic method for the preparation of $CH_3SnCl_3$ no longer optimal.

The aforementioned reaction of $SnCl_2$ with $CH_3Cl$ at a temperature of 365°C. (Smith et al., loc. cit.) proceeds with too small a yield (less than 1 gram per hour).

The present invention, thus, has as its object a technically useful process for the preparation of methyltin trichloride of high purity and in better yields.

According to the invention, this object has been achieved by carrying out the reaction of $SnCl_2$ with $CH_3Cl$ in a salt melt.

A feature of the invention, thus, is a process for the preparation of methyltin trichloride by the reaction of methyl chloride with molten tin-(II)-chloride wherein the reaction is carried out in a melt of one or more chlorides of the metals of the first to third main groups and of the first and second sub-groups of the Periodic System as solvents.

In a preferred embodiment of the invention, the reaction is carried out in a mixture, suitably a binary mixture, of chlorides of the aforementioned metals, particularly in a melt of $NaAlCl_4$ or $KAlCl_4$.

The principal properties of the salts or salt mixtures suitable for use according to the process of the invention are as follows:

1. the $SnCL_2$ should be soluble in the melt of salt or salt mixture in a suitable concentration range;
2. the melt should not begin to crystallize at temperatures above 260°C.;
3. the boiling point or sublimation point of the salt or salt mixture should be above the reaction temperature;
4. the salt or salt mixture must neither react with $CH_3Cl$ nor alter the oxidation state of the tin in $SnCl_2$.

Taking these requirements into account, the following salts are exemplary of those particularly suitable for carrying out the process of the invention: LiCl, NaCl, KCl, $MgCl_2$, $AlCl_3$, CuCl, $ZnCl_2$, and mixtures of these salts, particularly $NaAlCl_4$. The temperature of the reaction is determined, on the one hand, by the temperature at which crystallization of the melt begins and, on the other hand, by the boiling point or sublimation point of the salt or salt mixture and by the thermal stability of the reaction product. The temperature range between 250°C. and 300°C., particularly between 260°C. and 280°C. is advantageous.

The amount of the $SnCl_2$ dissolved in the melt of the salt or salt mixture exerts a considerable influence on the yield of $CH_3SnCl_3$. For example, in the preferred embodiment in which $NaAlCL_4$ is employed as the melt, the amount of dissolved $SnCl_2$ is about 40 mol percent. The maximum yield curve achieved at this concentration of the melt is very flat, so that the 40 mol percent $SnCl_2$ content of the melt need not be exactly maintained during the course of the reaction. There is very little decrease in yield when the concentration of $SnCl_2$ is in the range between 30 mol percent and 45 mol percent.

It is particularly advantageous to prepare the anhydrous $SnCl_2$ necessary for the process of the present invention in situ in the salt melt by the reaction of molten tin with $SnCl_4$. For this purpose, a definite amount of, for example, $NaAlCl_4$ is melted in a suitable vessel and is combined at a temperature of 260°–280°C. with a definite amount of metallic tin. Then, with the aid of a nitrogen stream, with stirring using a gasification stirrer [M. Zlokarnik, Ullmanns Enzyklopaedie der technischen Chemie, Vol. 2, 4th Edition, pages 259-281, Verlag Chemie, Weinheim/Bergstrasse, Germany (1972)], an amount of $SnCl_4$ is introduced such that the total amount of metallic tin is consumed. The amounts of metallic tin and $SnCl_4$ are so chosen that the melt contains 40 mol percent of $SnCl_2$ after conclusion of the reaction.

The preparation of such melts can, however, also be achieved simply by combination of anhydrous components in the above-described desired proportions.

The following Table shows suitable salt mixtures, their melting point, and advantageous concentrations of tin-(II)-chloride.

| Melt | Melting Point (°C) | SnCl$_2$ Content (Mol Percent) |
| --- | --- | --- |
| NaAlCl$_4$ | 152 | 25 – 60 |
| KZnCl$_3$ | 250 | 50 – 70 |
| ZnCl$_2$ | 318* | 40 – 60 |
| CuAlCl$_4$ | 233 | 60 – 90 |
| KAlCl$_4$ | 257 | 40 – 90 |

*The melting point of a eutectic mixture containing 56 mol percent of SnCl$_2$ is 171°C.

Preferably at a temperature between 270°C. and 280°C., CH$_3$Cl is now introduced into the prepared melt with stirring using a gasification stirrer. Excess CH$_3$Cl and the reaction product are transferred by means of a heated distillation bridge into a first vessel cooled with ice water and are cooled to room temperature. The major portion of the reaction product collects in this vessel. In a second receiver, also cooled with ice water, excess CH$_3$Cl is freed from further, entrained, reaction product and is subsequently condensed in a low-temperature receiver before it is reintroduced into the reaction.

A particularly advantageous embodiment of the reaction of the present invention can be carried out by recycling the methyl chloride. For this purpose, the excess CH$_3$Cl emerging from the end of the apparatus is re-introduced into the input of the apparatus with the aid of a membrane compresser. The amount of CH$_3$Cl consumed is continuously supplemented by introduction through a T-connector in this system. In this manner, the course of the reaction can be observed and controlled at any point in time.

A better understanding of the present invention and of its many advantages will be had by referring to the following specific examples given by way of illustration.

EXAMPLE 1 a. Preparation of the Melt

Under a dry inert gas atmosphere (N$_2$), a mixture of 304 g (5.2 mol) of dry NaCl, 693 g (5.2 mol) of anhydrous AlCl$_3$, and 208 g (1.75 mol) of tin are introduced into a cylindrical glass vessel having a volume of 3 liters and equipped with a ground glass cover having a central opening (NS 29) for a stirrer and three smaller openings (NS 19). A gasification stirrer, a reflux condenser with an attached bubble counter and CaCl$_2$-drying tube, and a nitrogen introduction tube are inserted in the openings in the cover. The fourth opening is then sealed with a stopper and the so-equipped cover is placed on the vessel which is then heated with the aid of an electrically-heated air bath to 270°–280°C. After the contents of the vessel have become liquid, the gasification stirrer is introduced deep enough into the melt that its exit openings are in the liquid tin. Then the nitrogen introduction tube and the stopper are replaced by two glass tubes, one of which is open at its lower end and serves as an input tube for SnCl$_4$. SnCl$_4$ is present in a pressure-equalized dropping funnel connected with this tube, from which it drops into the hot input tube through a three-way stopper in the pressure equalizing line and is then led into the melt with a nitrogen stream. The other glass tube is closed at the bottom and is used as a dip tube containing a resistance thermometer. The two glass tubes hinder the formation of a liquid stream which would otherwise be formed because of the rapidly turning stirrer.

Now, a weak nitrogen stream is introduced into the apparatus, the stirrer is brought to a velocity of 1200–1500 rpm, and the dropwise addition of SnCl$_4$ is begun. In particular, 456 g (1.75 mol) of SnCl$_4$ are added at a temperature of 270°–280°C. Addition is completed after three or four hours. The melt should then contain 40.2 mol percent of SnCl$_2$, corresponding to an Sn-content of 25 weight percent. A value of 24.6 weight percent was actually determined.

b. Reaction of SnCl$_2$ with CH$_3$Cl

The reflux condenser is now replaced by a distillation bridge connected with two ice-cooled receivers and bubble counters, two cold traps (−70°C.), and a flow measuring device. (The distillation bridge should be heatable to a temperature of 60°–80°C., i.e. the temperature should be above the melting point of the reaction product). Nitrogen is replaced by CH$_3$Cl. Then, the exit of the flow-measuring device is connected with the input of a membrane compressor of variable r.p.m., the output of which is connected by means of a T-connector to the input tube of the reactor. The CH$_3$Cl circulating in the system is continually supplemented through the T-connector according to its use by means of a pressure-regulated introduction of fresh CH$_3$Cl. With the aid of this arrangement, CH$_3$Cl is introduced into the apparatus at an excess of 30–60 mm Hg gauge and the gasification stirrer and the compressor are started. The stirring speed is set at 1200–1500 rpm and the capacity of the compressor is adjusted to 1–1.5 liters per minute. After a short time the reaction product accumulates, principally in the first receiver. The second receiver and the two cold traps serve to free the circulating CH$_3$Cl stream from entrained reaction product.

After 3.5–4 hours, about 300 g of CH$_3$SnCl$_3$ are formed (75–86 g/h). The consumption of CH$_3$Cl is 70 g. The melt has a tin content of 18.4 weight percent (calculated: 18.8 weight percent). Accordingly, the yield amounts to 85 percent, calculated on CH$_3$Cl, and of 98 percent, calculated on SnCl$_2$.

Time yields, measured over 3–6 hours, vary for different batches between 50 g/h and 130 g/h.

The product is of high purity and has a melting point of 44°–45°C. The content of CH$_3$SnCl$_3$ is 96–98 weight percent. The residue comprises equal parts of (CH$_3$)$_2$SnCl$_2$ and SnCl$_4$.

Now the initial conditions of the melt are again reproduced either (1) by the addition of an amount of anhydrous SnCl$_2$ determined from the amount of CH$_3$SnCl$_3$ earlier obtained, or (2) by the addition of Sn and SnCl$_4$ as described above under (a). As a control, the Sn content of the melt can be determined and should be between 24 weight percent and 25 weight percent. After 250 hours of operation, the melt was still entirely useful.

EXAMPLE 2

A mixture of 693 g (5.2 mol) of anhydrous AlCl$_3$ and 664 g (3.5 mol) of anhydrous SnCl$_2$, coated with 304 g (5.2 mol) of dry NaCl, is melted in the reaction vessel described in 1(a). The process is then carried out as in Example 1(b) above.

EXAMPLES 4–11

Proceeding as in Example 2, but using other melt systems, CH$_3$Cl is introduced into these melts according to Example 1(b) or Example 3. The results are summarized in the Table below.

EXAMPLE 3

CH$_3$Cl is introduced according to Example 1(b) into a melt prepared according to Example 1 or Example 2 with the difference that the CH$_3$Cl is not circulated with the aid of a membrane compressor. Rather, excess CH$_3$Cl is condensed at the end of the apparatus train in a cold trap (−70°C.).

TABLE

| Example No. | Melt and Melting Point | Preparation | SnCl$_2$ Content (Mol Percent) | Average Yield (g/h) |
|---|---|---|---|---|
| 4 | CuAlCl$_4$ (233°C.) | 1046 g (7.8 mol) AlCl$_3$<br>755 g (7.8 mol) CuCl | 90 – 60 | 40 |
| 5 | KAlCl$_4$ (257°C.) | 1033 g (7.7 mol) AlCl$_3$<br>575 g (7.7 mol) KCl | 90 – 40 | 65 |
| 6 | KZnCl$_3$ (250°C.) | 1675 g (12.3 mol) ZnCl$_2$<br>915 g (12.3 mol) KCl | 70 – 50 | 20 |
| 7 | ZnCl$_2$ (318°C.)* | 1300 g (9.5 mol) ZnCl$_2$ | 60 – 40 | 30 |
| 8 | LiAlCl$_4$ (ca. 151°C.) | 425 g (10 mol) LiCl<br>1333 g (10 mol) AlCl$_3$ | 75 – 25 | 45 |
| 9 | Ba(AlCl$_4$)$_2$ (ca. 290°C.) | 880 g (4.2 mol) BaCl$_2$<br>1120 g (8.4 mol) AlCl$_3$ | 90 – 70 | 27 |
| 10 | NaCl.3SnCl$_2$ (183°C.) | 300 g (5.1 mol) NaCl | 80 – 65 | 28 |
| 11 | KCl.3SnCl$_2$ (208°C.) | 300 g (4.0 mol) KCl | 80 – 65 | 28 |

*The melting point of a eutectic mixture containing 56 mol percent of SnCl$_2$ is 171°C.

What is claimed is:

1. In a method for making methyltin trichloride by reacting methyl chloride with molten tin-(II)-chloride, the improvement wherein said reagents are reacted in an anhydrous salt melt solvent at a temperature between 250°C. and 300°C. Under an inert atmosphere, said salt melt (1) being a solvent for said tin-(II)-chloride and containing from 25 to 90 mol percent of tin-(II)-chloride dissolved therein, (2) having an initial crystallization temperature above 260°C., (3) having a boiling or sublimation temperature above the reaction temperature, (4) being inert to reaction with CH$_3$Cl and not altering the oxidation state of the tin in SnCl$_2$, and (5) consisting essentially of at least one chloride of a metal selected from the group consisting of metals of the first to third main groups and metals of the first and second sub-groups of the Periodic System.

2. A method as in claim 1 which is performed continuously.

3. A method as in claim 1 which is performed discontinuously.

4. A method as in claim 1 wherein said salt melt consists essentially of at least one chloride of a metal selected from the group consisting of Li, Na, K, Ba, Mg, Al, Cu, and Zn.

5. A method as in claim 1 wherein said salt melt is a binary mixture of said chlorides.

6. A method as in claim 1 wherein said salt melt is NaAlCl$_4$.

7. A method as in claim 1 wherein said salt melt is KAlCl$_4$.

8. A method as in claim 1 wherein said tin-(II)-chloride is formed in situ in said salt melt by the reaction of molten tin with tin tetrachloride under an inert atmosphere.

* * * * *